US012642643B2

(12) United States Patent
Riopelle et al.

(10) Patent No.: US 12,642,643 B2
(45) Date of Patent: Jun. 2, 2026

(54) METHODS AND APPARATUSES FOR ATTACHING HAIR USING SURGICAL THREAD

(71) Applicant: Jeffrey Riopelle, Meadow Vista, CA (US)

(72) Inventors: Jeffrey Riopelle, San Ramon, CA (US); Mark Thomas, Cupertino, CA (US)

( * ) Notice: Subject to any disclaimer, the term of this patent is extended or adjusted under 35 U.S.C. 154(b) by 74 days.

(21) Appl. No.: 18/829,141

(22) Filed: Sep. 9, 2024

(65) Prior Publication Data

US 2024/0423780 A1 Dec. 26, 2024

Related U.S. Application Data

(62) Division of application No. 18/581,949, filed on Feb. 20, 2024, now Pat. No. 12,114,718.

(Continued)

(51) Int. Cl.
*A61F 2/10* (2006.01)
*A41G 5/00* (2006.01)
(Continued)

(52) U.S. Cl.
CPC .............. *A61F 2/10* (2013.01); *A41G 5/0066* (2013.01); *A41G 5/0086* (2013.01); *A61B 17/00* (2013.01); *A61B 17/3468* (2013.01); *A61B 2017/00752* (2013.01); *A61B 17/06066* (2013.01); *A61B 2017/0608* (2013.01); *A61B 2017/061* (2013.01); *A61B 2017/06176* (2013.01); *A61B 2017/3454* (2013.01); *A61F 2220/0016* (2013.01)

(58) Field of Classification Search
CPC ........ A61B 17/3468; A61B 2017/0608; A61B 2017/061; A61B 2017/06176; A61B 2017/3454; A61F 2220/0016
See application file for complete search history.

(56) References Cited

U.S. PATENT DOCUMENTS

| | | |
|---|---|---|
| 3,553,737 A | 1/1971 | Bauman |
| 4,254,772 A | 3/1981 | McNamee |

(Continued)

FOREIGN PATENT DOCUMENTS

WO 2024177908 A1 8/2024

OTHER PUBLICATIONS

International Search Report and Written Opinion for International Patent Application No. PCT/US24/16300, mailed 20240617, 11 pages.

(Continued)

*Primary Examiner* — Ashley L Fishback
(74) *Attorney, Agent, or Firm* — Elliott, Ostrander & Preston, P.C.

(57) ABSTRACT
A human hair implant procedure involves inserting a length of barbed surgical thread through a cannula so that a first portion including a distal end of the barbed surgical thread is near a distal end of the cannula and a second portion is outside the proximal end of the cannula, then inserting the distal end of the cannula through an entry point of the skin of the human and advancing the cannula under the skin until the proximal end of the cannula is near the entry point of the skin. Then, removing the cannula from under the skin, leaving in position under the skin the first portion of barbed surgical thread which secures a hold to tissue under the skin, and finally, attaching hair to the second portion of barbed surgical thread.

6 Claims, 15 Drawing Sheets

Related U.S. Application Data

(60) Provisional application No. 63/447,007, filed on Feb. 20, 2023.

(51) Int. Cl.
| | |
|---|---|
| *A61B 17/00* | (2006.01) |
| *A61B 17/06* | (2006.01) |
| *A61B 17/34* | (2006.01) |

(56) References Cited

U.S. PATENT DOCUMENTS

| | | | |
|---|---|---|---|
| 4,583,540 | A | 4/1986 | Malmin |
| 5,330,530 | A | 7/1994 | Hastings |
| 5,693,064 | A | 12/1997 | Arnold |
| 6,468,288 | B1 | 10/2002 | Manning |
| 2005/0240224 | A1 | 10/2005 | Wu |
| 2011/0048445 | A1 | 3/2011 | Lee |
| 2016/0050997 | A1 | 2/2016 | Ott |
| 2017/0135713 | A1 | 5/2017 | Suh et al. |
| 2018/0168709 | A1 | 6/2018 | Allison |
| 2024/0277093 | A1 | 8/2024 | Riopelle et al. |
| 2024/0277466 | A1 | 8/2024 | Riopelle et al. |

OTHER PUBLICATIONS

Notice of Allowance for U.S. Appl. No. 18/444,543, mailed Apr. 25, 2024, 10 pages.
Notice of Allowance for U.S. Appl. No. 18/581,949, mailed Jun. 11, 2024, 13 pages.

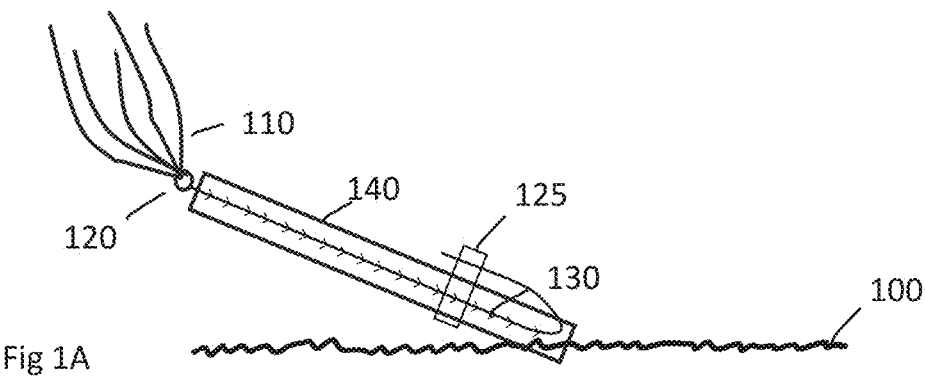
Fig 1A
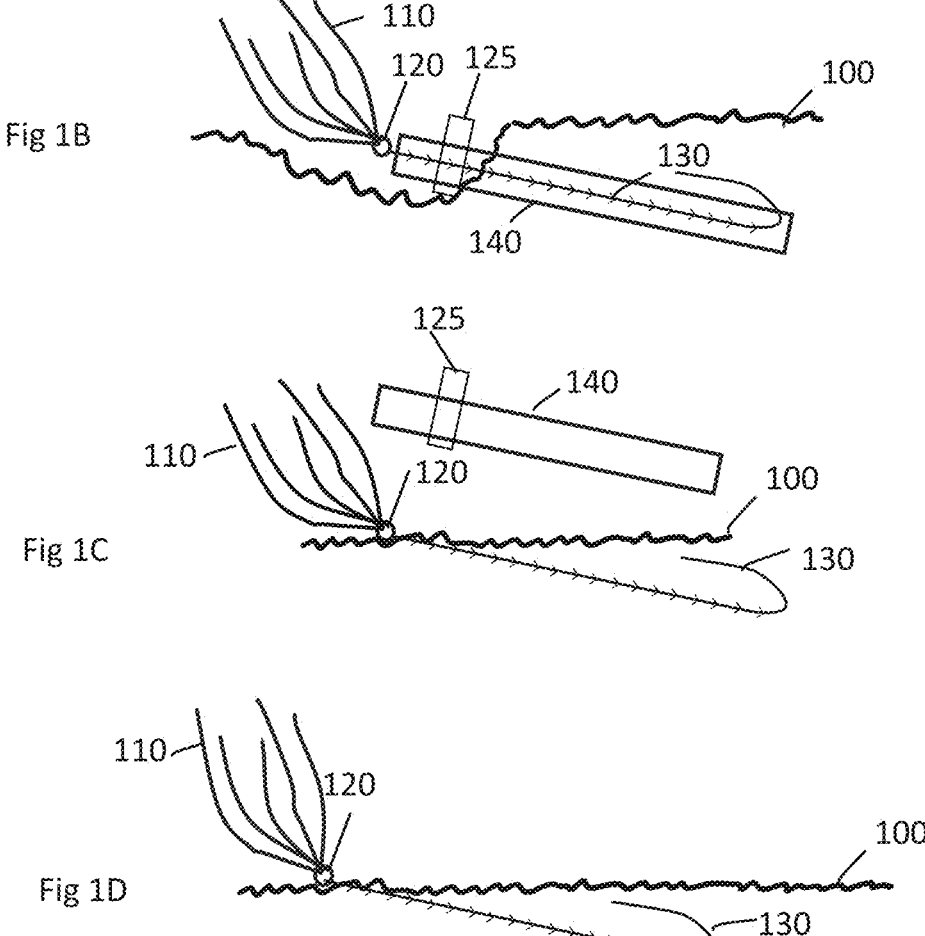
Fig 1B
Fig 1C
Fig 1D

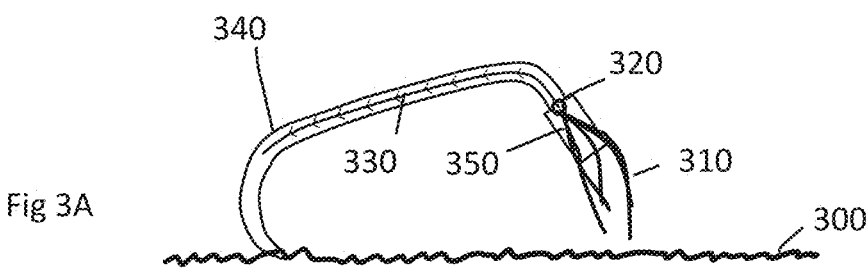
Fig 3A
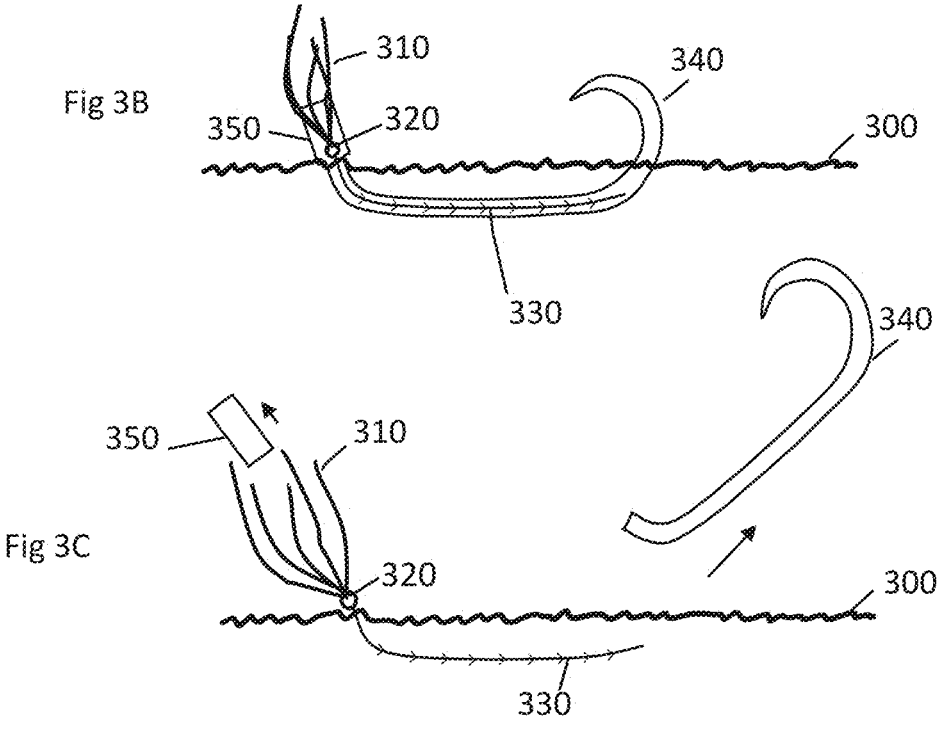
Fig 3B
Fig 3C
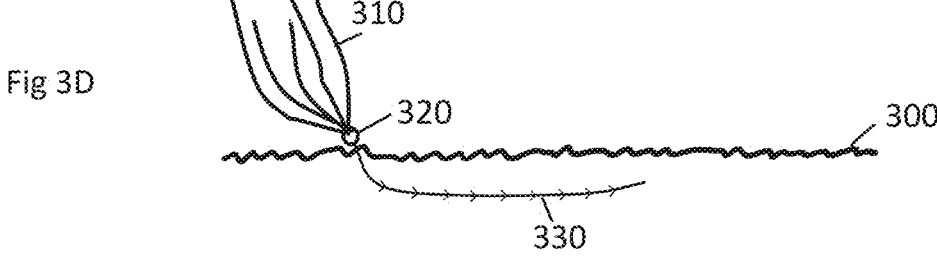
Fig 3D

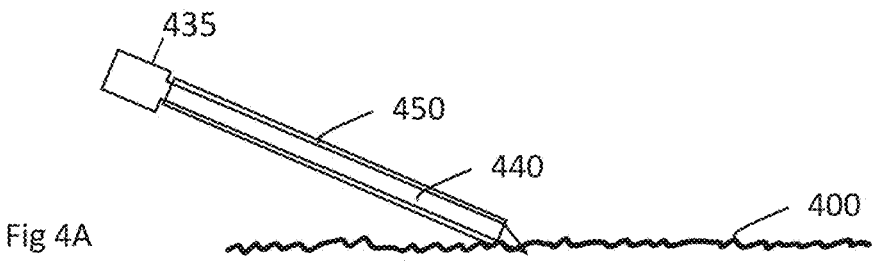
Fig 4A
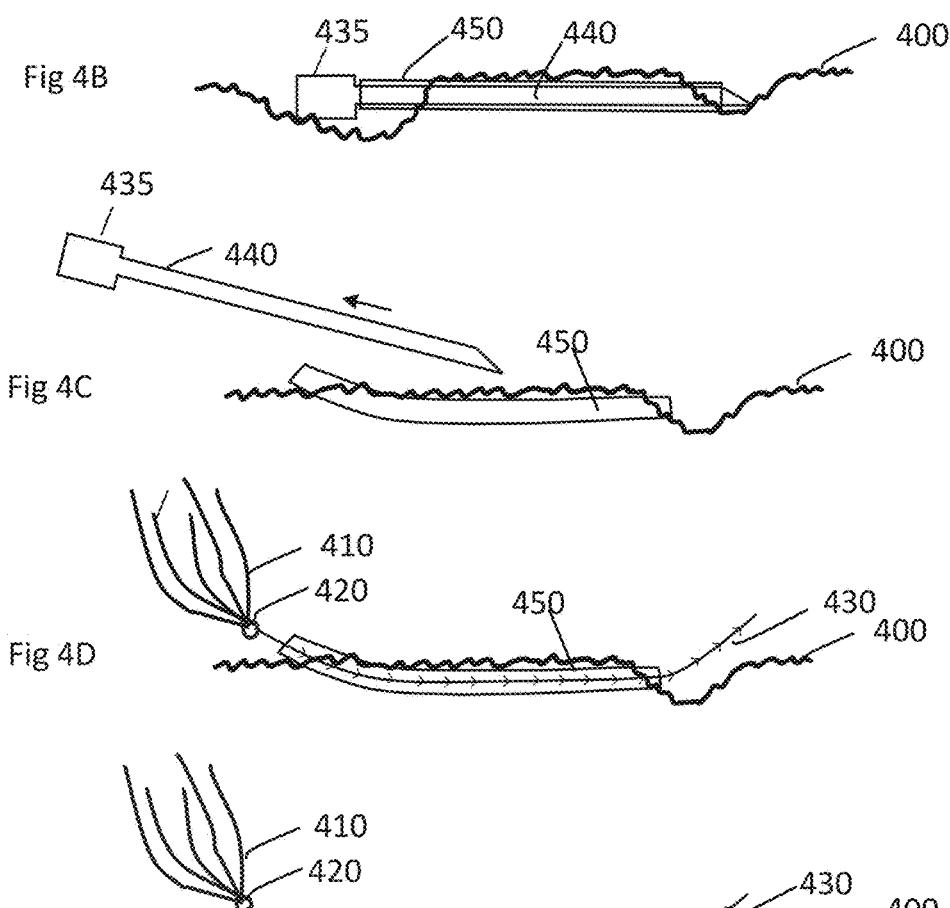
Fig 4B
Fig 4C
Fig 4D
Fig 4E
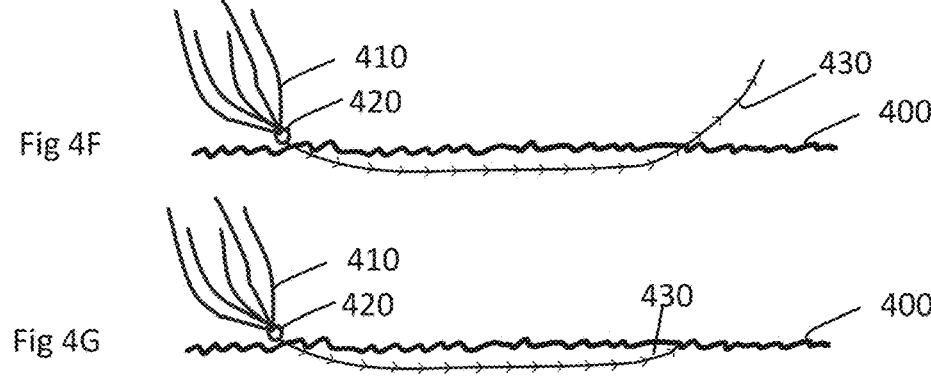
Fig 4F
Fig 4G

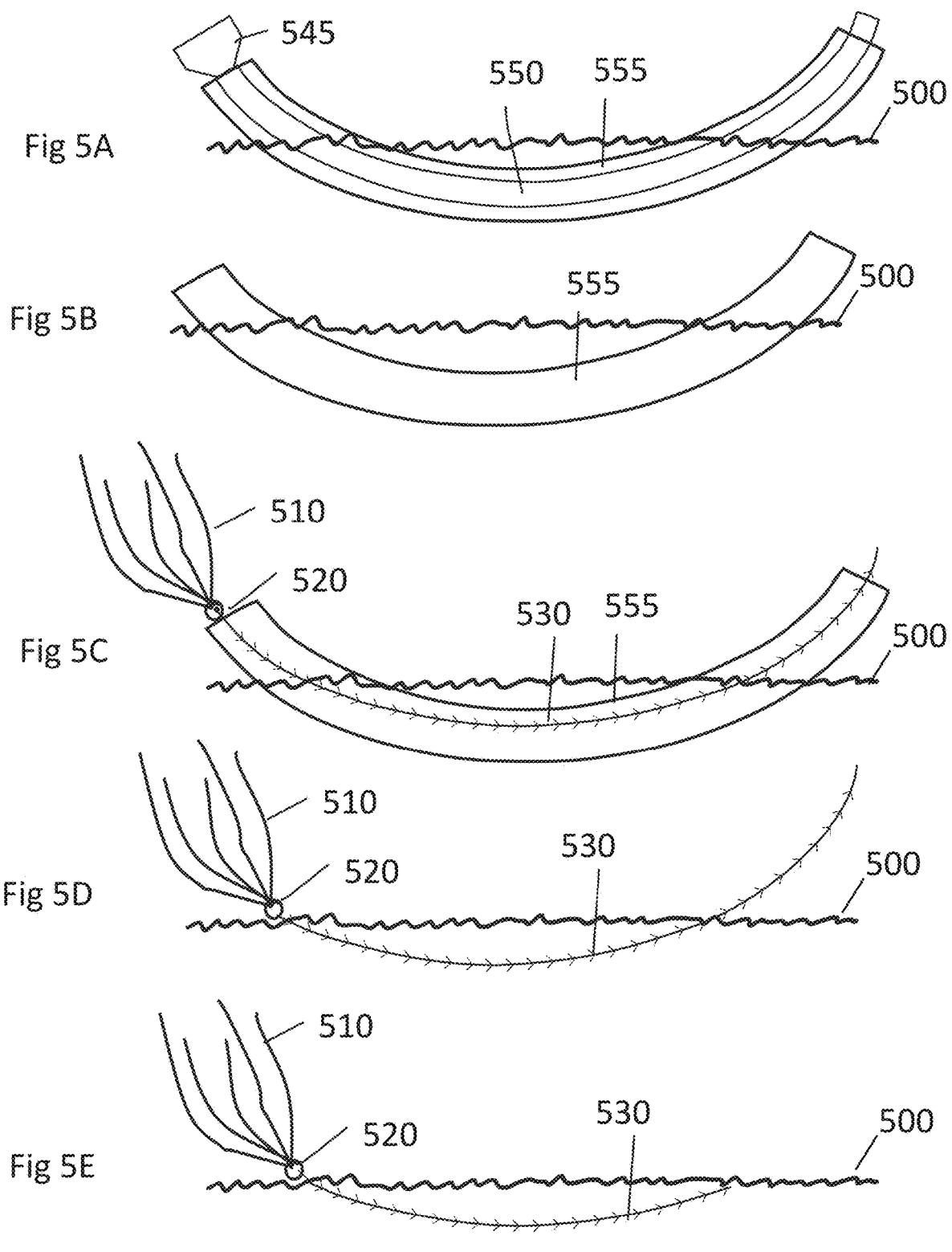

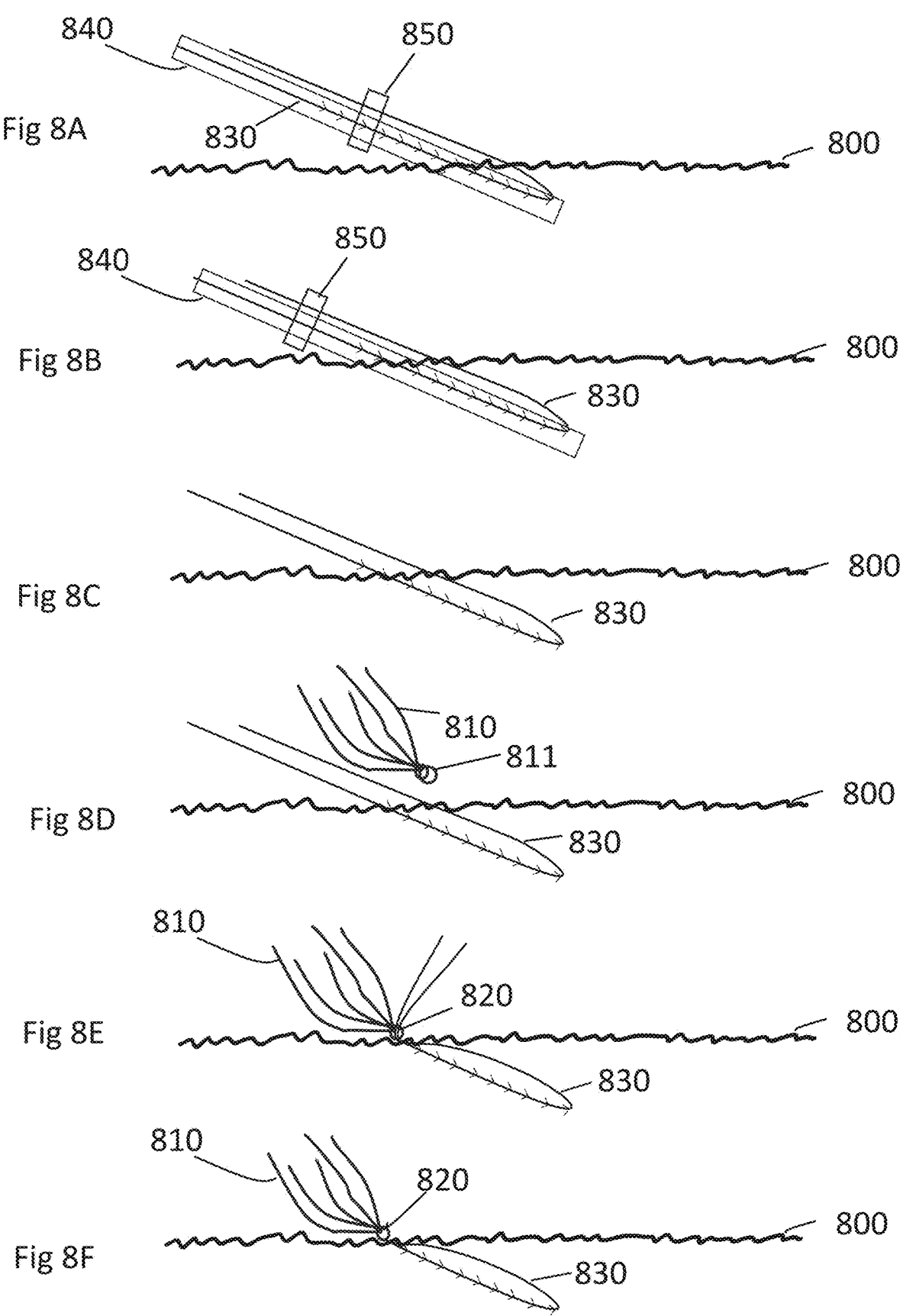

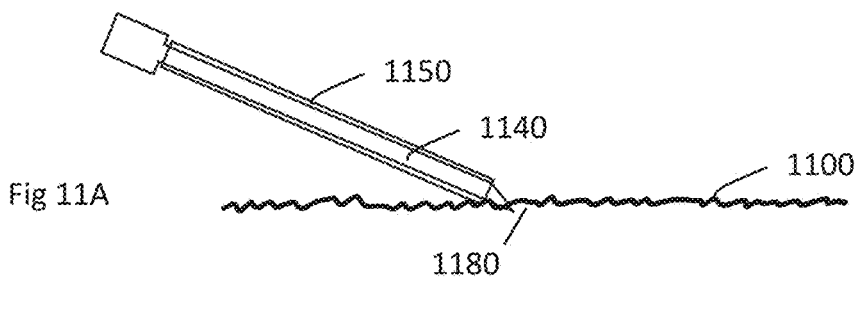
Fig 11A
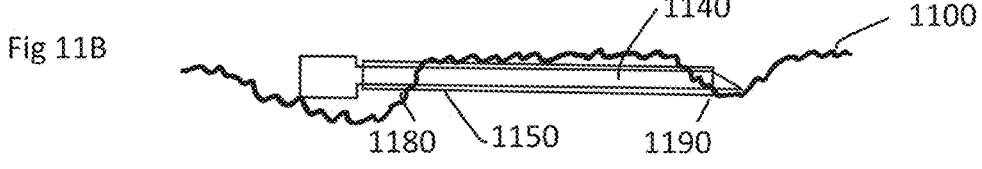
Fig 11B
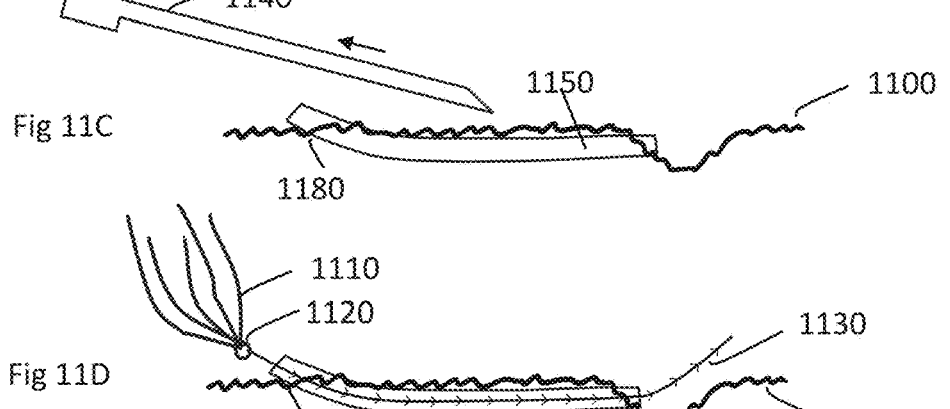
Fig 11C
Fig 11D
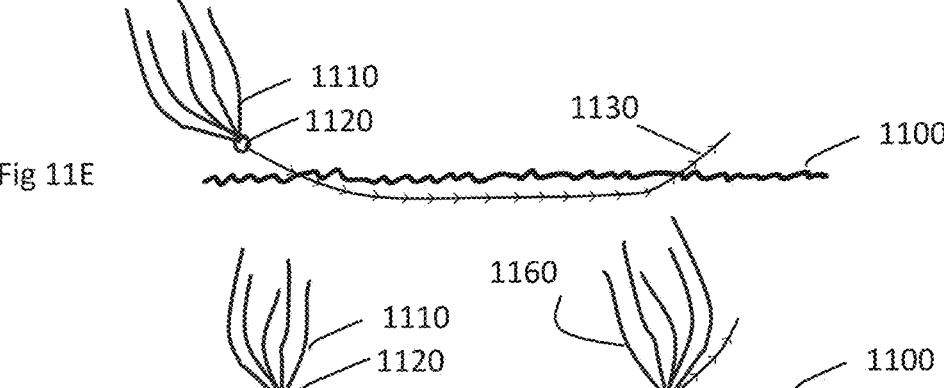
Fig 11E
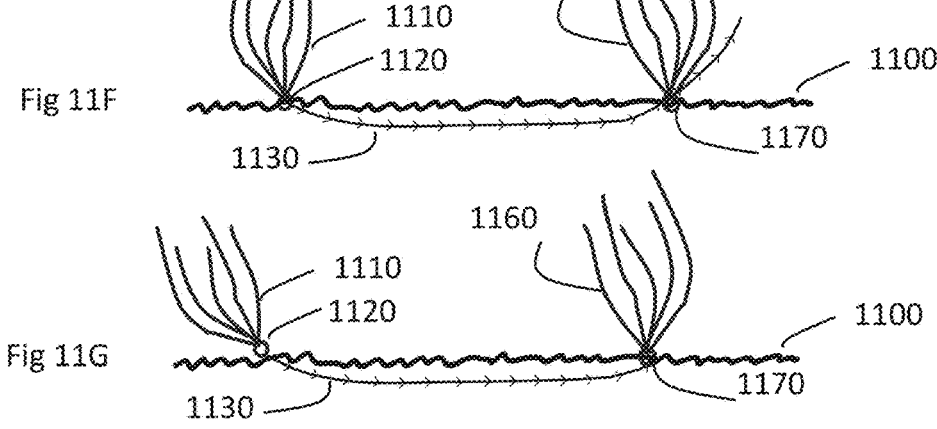
Fig 11F
Fig 11G

METHODS AND APPARATUSES FOR ATTACHING HAIR USING SURGICAL THREAD

CROSS REFERENCE TO RELATED DOCUMENTS

This non-provisional application is a divisional of U.S. patent application Ser. No. 18/581,949 filed Feb. 20, 2024, which claims the benefit under 35 U.S.C. 119 (e) of U.S. provisional patent application No. 63/447,007 filed Feb. 20, 2023, entitled "Methods and Apparatuses for Hair Extension System Using Surgical Thread Attachments", the entire contents of which are incorporated herein by reference.

TECHNICAL FIELD

Embodiments of the invention relate to attaching hair to the skin of a human using surgical thread to which the hair is coupled at one end.

BACKGROUND

Traditional hair extensions are lengths of real or synthetic hair that are typically attached to a person's existing hair. There are a number of variations of these types of hair extension techniques, based on the means of integrating or attaching the hair extensions with the person's existing hair. The attachment mechanisms include simple clips, tape, glue, microbeads, etc. Properly applied, the effect achieved can be outstanding. However, there are several shortcomings to these hair extension techniques. First, hair extensions require constant maintenance and may need to be redone every month or so. Second, for best results, the hair extensions should be performed by a professional and thus may be very costly per session. Multiplying the cost per session by the number of sessions per year yields an annual cost which may exceed several thousand dollars. In addition, the annual amount of the person's time to undergo such procedures is likely to be in excess of 30 hours per year. Third, and perhaps most important, attachment of hair extensions may lead to existing hair loss.

BRIEF DESCRIPTION OF THE DRAWINGS

The detailed description is set forth with reference to the accompanying figures. In the figures, the left-most digit(s) of a reference number identifies the figure in which the reference number first appears. The use of the same reference numbers in different figures indicates similar or identical items or features.

FIGS. 1A, 1B, 1C, and 1D are a series of diagrams showing a sequence of operational steps to implant hair in accordance with an embodiment of the invention.

FIGS. 3A, 3B, 3C, and 3D are a series of diagrams showing the sequence of operational steps to implant hair in accordance with an embodiment of the invention.

FIGS. 4A, 4B, 4C, 4D, 4E, 4F, and 4G are a series of diagrams showing the sequence of operational steps to implant hair in accordance with an embodiment of the invention.

FIGS. 5A, 5B, 5C, 5D, and 5E are a series of diagrams showing the sequence of operational steps to implant hair in accordance with an embodiment of the invention.

FIGS. 8A, 8B, 8C, 8D, 8E, and 8F are a series of diagrams showing the sequence of operational steps to implant hair in accordance with an embodiment of the invention.

FIGS. 10A, 10B, and 10C are a series of diagrams showing the sequence of operational steps to implant hair in accordance with an embodiment of the invention.

FIGS. 11A, 11B, 11C, 11D, 10E, 11F, and 11G are a series of diagrams showing the sequence of operational steps to implant hair in accordance with an embodiment of the invention.

DETAILED DESCRIPTION

Embodiments of the invention relate to implanting hair on a human. The embodiments use barbed (or equivalent) surgical threads inserted under the skin 100, for example, under the scalp, of a person as an anchor to which to attach hair as shown in FIGS. 1A-1D. There are two anchoring methods according to the disclosed embodiments.

The first method uses a barbed surgical thread 130 inserted under the skin 100 as an anchor to which to attach hair 110. The hair 110 may be a plurality of strands of artificial or real human hair whose length, thickness, color and number are selectable. The barbed surgical thread 130 is similar to or the same as those currently used in a thread lift, a cosmetic procedure that uses thread to sculpt the face or breasts. A thread lift uses absorbable, barbed sutures to allegedly tighten one's skin by inserting medical-grade thread material into the face or breasts and then pulling up the skin by tightening the thread.

There are many types of barbed surgical threads on the market today, varying in material and contour, or shape, and location, angle, and number of barbed structures, including PDO (polydioxanone), PLA (polylactic acid), and PCA (polycaprolactone). Other materials include polyethylene terephthalate (by Merceline), nylon, polypropylene, polyethylene, polyester, PDO (polydioxanone on cotton), and silk. The important characteristics of these surgical threads are: (1) the threads have a barb-like structure that provide smooth tissue passage and a secure hold that helps control tension and achieve excellent tissue approximation, in other words, it makes the threads easy to insert but resist retraction, (2) they dissolve slowly over a period of approximately 3 to 8 months (depending on the specific materials and design) and typically result in minimal scarring. Characteristic (1) is important for providing the anchoring function according to embodiments of the invention without the need to tie a surgical knot. Hereinafter references to barbed surgical thread is meant to encompass any such surgical thread that provides knotless tissue control, that is, any such surgical thread that eliminates the need for surgical knot tying while attaching hair to a human according to the disclosed embodiments. Equivalent terms for barbed surgical thread, for the purposes of the embodiments of the invention disclosed herein, is knotless surgical thread, or a knotless tissue control device.

A connector or fastener 120 attaches the hair to a proximal end of the barbed surgical thread. The connector may include one or more of glue, a mechanical crimp, chemical fusion, and micro-connectors of various designs.

Figures 13A, 13B, 13C, 13D, 13E:
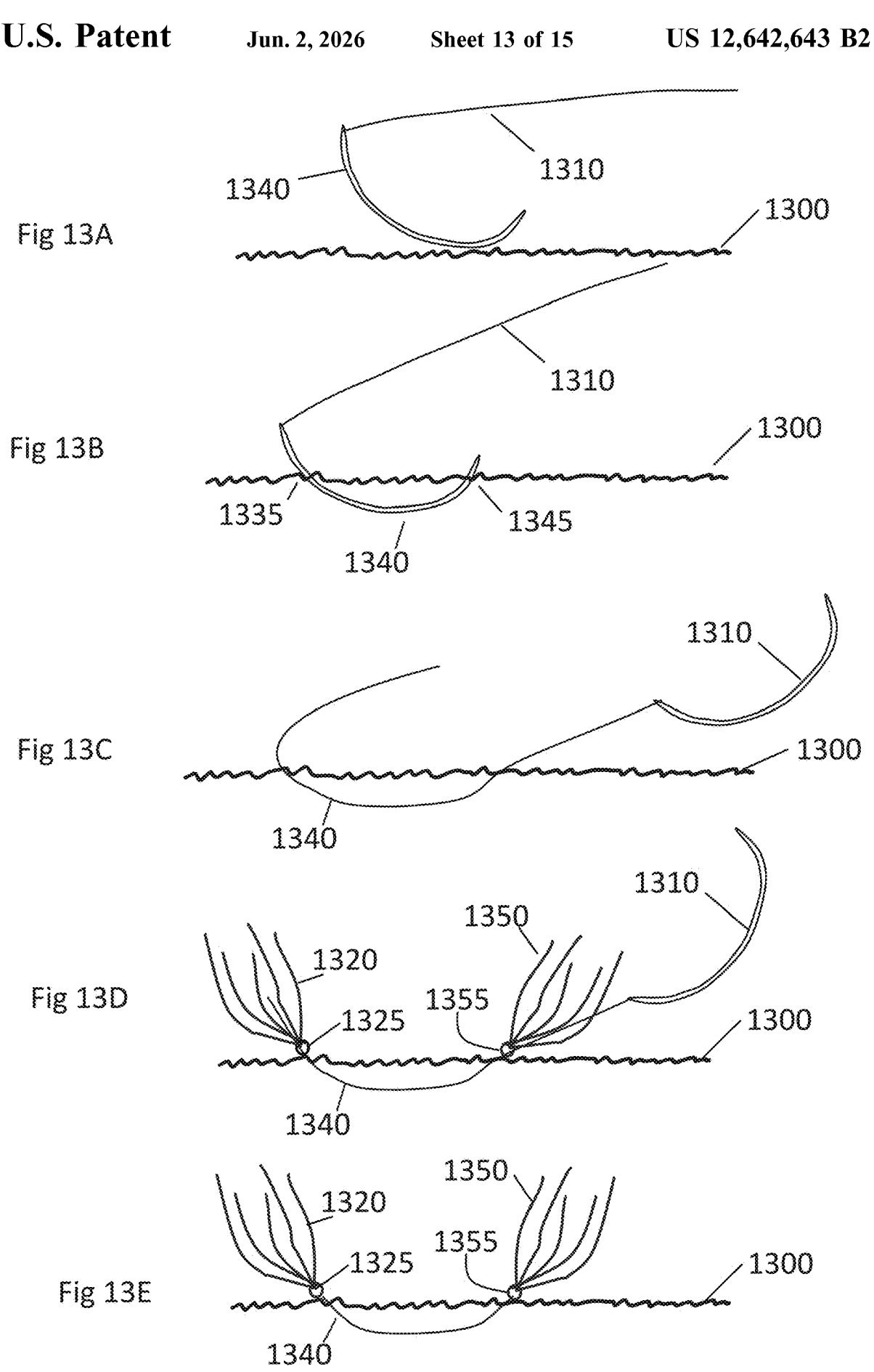
FIGS. 13A, 13B, 13C, 13D, and 13E are a series of diagrams showing the sequence of operational steps to implant hair in accordance with an embodiment of the invention.
Figures 14A, 14B, 14C, 14D:
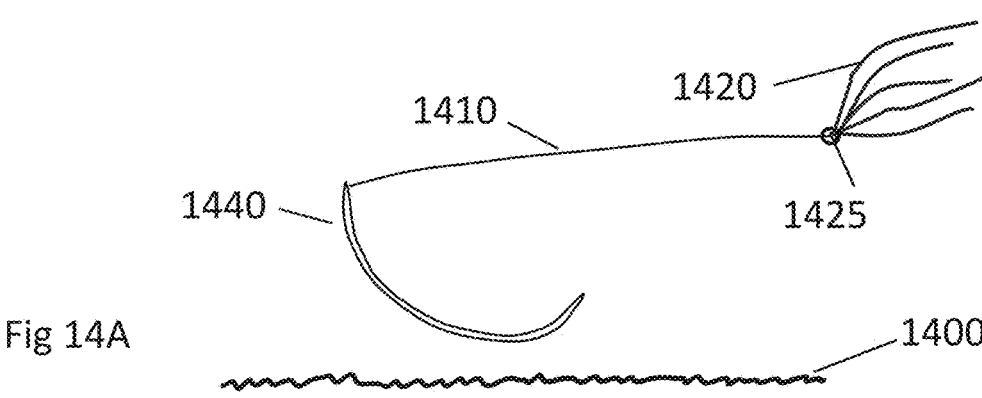
FIGS. 14A, 14B, 14C, and 14D are a series of diagrams showing the sequence of operational steps to implant hair in accordance with an embodiment of the invention.
Figures 15A, 15B, 15C, 15D:
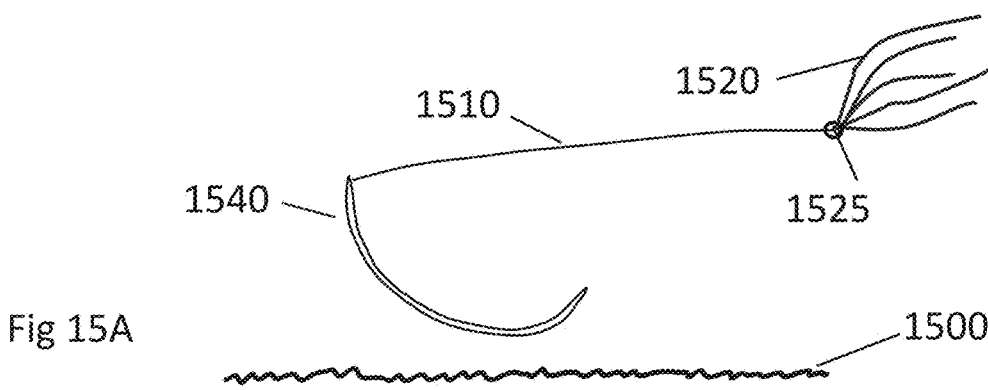
FIG. 15A, FIG. 15B, FIG. 15C, and FIG. 15D are a series of diagrams showing the sequence of operational steps to implant hair in accordance with an embodiment of the invention.

The second method uses the barbed surgical thread 130 or smooth thread inserted under the skin 100 to which to attach hair 110 at both ends of the thread such as shown in FIG. 13E. In FIG. 13E, the two hair attachments 1320 and 1350 are connected by a surgical thread 1310. Any attempt to remove the first hair attachment 1320 will be resisted by the second hair attachment 1350 that it is connected to surgical thread 1310. Reciprocally, any attempt to remove the second hair attachment 1350 will be resisted by the first hair attachment 1320 that it is connected to surgical thread 1310.

As more fully described below, many of the disclosed embodiments include:

(1) a means of attaching hair to a surgical thread,
(2) a means of inserting the thread under the skin,
(3) a means of extracting the insertion means,
(4) a means for advancing the surgical thread to the desired position, such that the connector between the surgical thread and the hair is positioned close to the skin of the person.

Embodiment 1 is illustrated in FIG. 1A, FIG. 1B, FIG. 1C, and FIG. 1D. These figures illustrate a set of operational steps and associated equipment for implanting hair. FIG. 1A shows a hair implant apparatus compromised of hair 110, connector 120, a surgical thread 130, a cannula 140, and a doughnut shaped elastomeric element 125 (slidably engaged with the exterior surface of the cannula and which holds the surgical thread that exits the distal end of the cannula and folds back along the exterior surface of the cannula), ready to be inserted under the skin 100. In FIG. 1B, the cannula 140 is inserted under the skin 100 until the connector 120 is nearly in contact with the skin 100. In FIG. 1C, the cannula is extracted. The cannula may be blunt or sharp tipped. If a blunt tip is used then it may be use a larger gauge needle (e.g., 18 gauge) to create an insertion hole. Extraction of the cannula involves the hair and connector passing through the interior cavity of the cannula. FIG. 1D shows the hair implant in its intended, final, position.

Thus, according to an embodiment of the invention, there is provided a method for attaching hair to a human, comprising: inserting a length of barbed surgical thread through a cannula so that a first portion including a distal end of the length of barbed surgical thread is near a distal end of the cannula and a second portion of the length of barbed surgical thread is outside the proximal end of the cannula; inserting the distal end of the cannula through an entry point of the skin of the human; advancing the cannula under the skin until the proximal end of the cannula is near the entry point of the skin; removing the cannula from under the skin, leaving in position under the skin the first portion of the length of barbed surgical thread which secures a hold to tissue under the skin; and attaching hair to the second portion of the length of barbed surgical thread. It is appreciated that sequence of steps in the method may be different than described above. For example, the hair may be attached to the second portion of the length of barbed surgical thread before or after any other step in the process.

Further, according to an embodiment of the invention, there is provided an apparatus comprising a cannula having an inner cavity, a proximal end, and a distal end; a length of barbed surgical thread, a first portion of which is positioned in the interior cavity of the cannula so that a distal end of the length of barbed surgical thread is near the distal end of the cannula, and a second portion of which is positioned outside the proximal end of the cannula; a connector; and hair coupled via the connector to the second portion of the length of barbed surgical thread, whereupon insertion and removal of the cannula from under the skin of a human leaves in position under the skin the first portion of the length of barbed surgical thread which secures a hold to tissue under the skin, and the connector in position above the skin, with the hair coupled thereto.

Figures 2A, 2B, 2C, 2D:
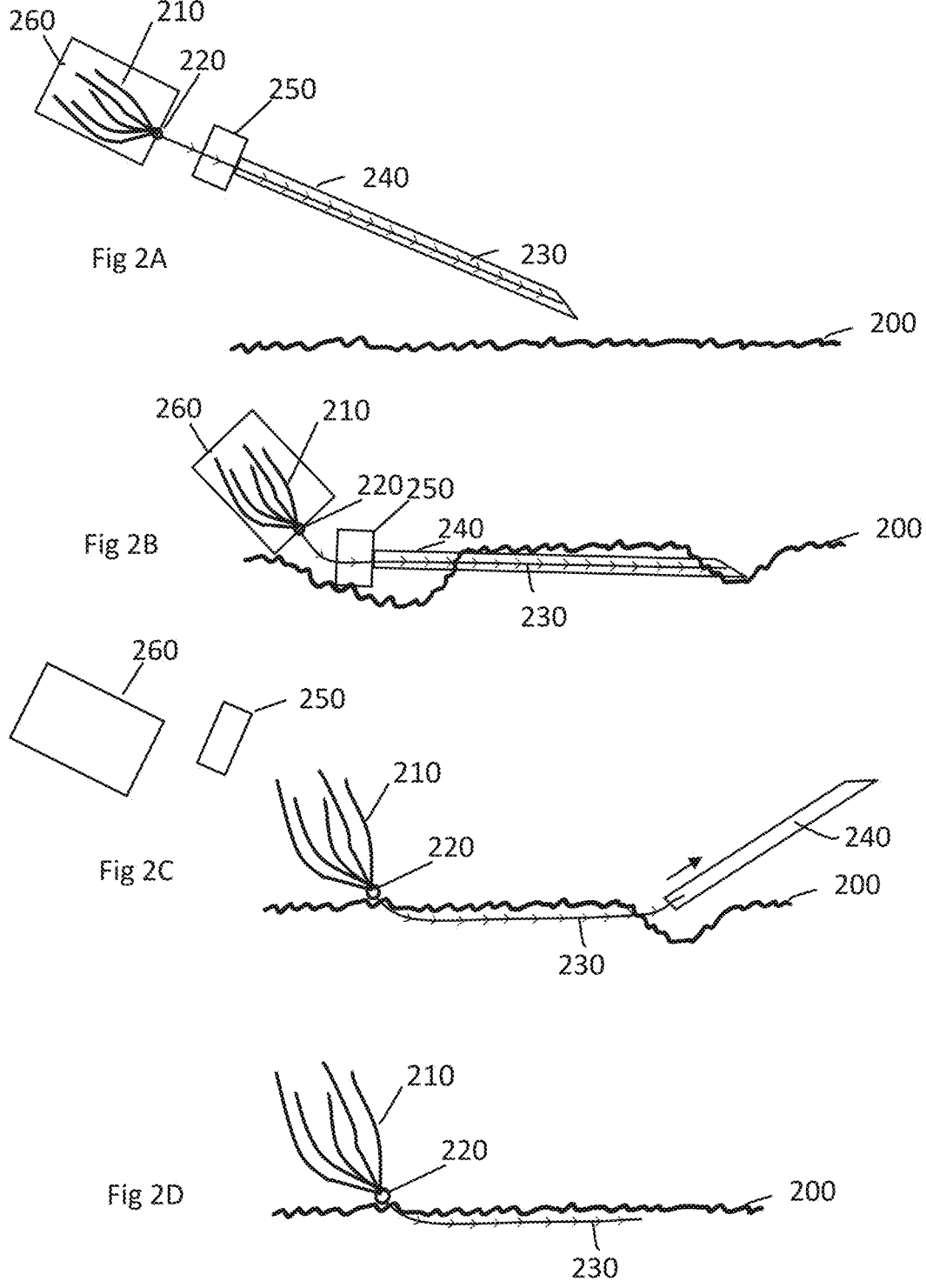
FIGS. 2A, 2B, 2C, and FIG. 2D are a series of diagrams showing a sequence of operational steps to implant hair in accordance with an embodiment of the invention.

Embodiment 2 is illustrated in FIG. 2A, FIG. 2B, FIG. 2C, and FIG. 2D. These figures illustrate a series of operational steps and associated equipment for implanting hair. FIG. 2A shows a hair implant apparatus (compromised of hair 210, connector 220, and a surgical thread 230) attached to a sharped tipped cannula 240, ready to be inserted under the skin 100. A handle 250 is attached to the cannula at the proximal end to aid in the control of the cannula during insertion. In addition, there is a protective cover 260 (e.g., a plastic cap or plastic bag) over the hair. The protective cover prevents damage or contamination during the assembly process and also secures the hair in a small volume that could otherwise interfere with the insertion process. In FIG. 2B the needle is inserted in the skin 200 by depressing the skin near the entrance point and then advancing the distal end of the cannula to exit, again enabled by depressing the skin near the exit point. In FIG. 2C both the protective cover over the hair is removed and the handle 260 is removed, then the cannula is removed through the exit point, and the remaining surgical thread is advanced until the connector 220 is either touching or nearly touching the skin. The extra surgical thread extending beyond the exit point is trimmed to be flush or beneath the skin surface. FIG. 2D shows the hair implant in position. One of the advantages of Embodiment 2 over Embodiment 1 is the extraction of the insertion tool does not interfere with the hair.

Thus, according to an embodiment of the invention, there is provided a method wherein the distal end of the cannula comprises a sharp tip, and wherein inserting the distal end of the cannula through an entry point of the skin of the human comprises the sharp-tipped distal end of the cannula piercing the skin of the human at the entry point; and removing the cannula from under the skin comprises the sharp-tipped distal end of the cannula piercing the skin of the human at an exit point that is different than the entry point, removing the handle from the proximate end of the cannula, and pulling on the distal end of the cannula at the exit point of the skin. Further, according to an embodiment of the invention, the apparatus comprising the cannula may include a handle removably coupled to the proximal end of the cannula, so that inserting the distal end of the cannula through an entry point of the skin and advancing the cannula under the skin until the proximal end of the cannula is near the entry point of the skin involves applying pressure on the handle of the cannula to effect insertion of the distal end of the cannula through the entry point of the skin and advancement of the cannula under the skin until the proximal end of the cannula is near the entry point of the skin. Additionally, a protective cover may encompass all or at least a portion of the hair which may be removed after removing the cannula from under the skin and attaching hair to the second portion of the length of barbed surgical thread.

Embodiment 3 is illustrated in FIG. 3A, FIG. 3B, FIG. 3C and FIG. 3D. These figures show a series of operational steps and associated equipment for implanting hair. This is essentially the same as Embodiment 2 except that a curved sharp tipped cannula 340 is used instead of straight sharp tipped cannula. FIG. 3A shows a hair implant apparatus (compromised of a hair 310, connector 320, and a surgical thread 330) attached to a curved cannula 340, ready to be inserted under the skin 300. In addition, there is a handle 350 attached to the proximal end of the cannula to facilitate the insertion process. In FIG. 3B the cannula is inserted in the skin 300 at the entrance point and then advancing the cannula, until the distal end of the curved cannula exits and the connector 320 is either touching or nearly touching the skin surface 300. In FIG. 3C the handle 350 is removed, then the cannula is removed through the exit point. One of the advantages of Embodiment 3 over Embodiment 2 is the insertion and extraction of the cannula does not require as much skin manipulation. Another advantage of Embodiment 3 over Embodiment 2 is that it is an effective method for high density installations. Thus, according to an embodiment of the invention, the proximal end, the distal end, or both ends of the cannula may be curved.

Embodiment 4 is illustrated in FIG. 4A, FIG. 4B, FIG. 4C, FIG. 4D, FIG. 4E, FIG. 4F, and FIG. 4G. These figures show a series of operational steps and associated equipment for implanting hair. FIG. 4A shows a sharp tipped cannula 440 and cannula handle 435, with a tube 450 attached (on the outside) prior to insertion under the skin 400. FIG. 4B shows the cannula 440 and the attached tube 450 inserted under the skin 400 and advance to an exit point. FIG. 4C shows the cannula 440 and cannula handle 435 removed and the tube 450 remaining, effectively creating a tunnel between an insertion opening and the exit opening. FIG. 4D shows a hair implant comprised of hair 410, a connector 420, and a surgical thread 430; where the surgical thread has been advanced through the proximal end of the tube 450 and exiting the distal end of the tube 450. In FIG. 4E, the tube is removed from the exit point leaving the surgical thread. In FIG. 4F the surgical thread 430 is advanced on the exposed distal end, until the connector 420 is either touching or nearly touching the skin 400. In FIG. 4G the surgical thread is trimmed at its distal end to be flush with or slightly below the skin.

Thus, according to an embodiment of the invention, there is provided a method for attaching hair to a human, comprising: inserting and advancing a sharp-tipped distal end of a cannula through an inner cavity of a flexible tube until the distal end of the cannula projects beyond a distal end of the tube; inserting the distal end of the cannula and the distal end of the tube through an entry point of the skin of the human; advancing the cannula and tube under the skin until a proximal end of the cannula and a proximal end of the tube is near the entry point of the skin and the sharp-tipped distal end of the cannula pierces the skin of the human at an exit point that is different than the entry point and the distal ends of the cannula and the tube project beyond the exit point; retracting the cannula from the tube via the proximal end of the tube, leaving the tube in position under the skin; inserting a length of barbed surgical thread through the tube so that a first portion of the length of barbed surgical thread extends through the tube and beyond the distal end of the tube and a second portion of the length of barbed surgical thread extends beyond the proximal end of the tube; removing the tube from under the skin, leaving in position under the skin the first portion of the length of barbed surgical thread which secures a hold to tissue under the skin; and attaching hair to the second portion of the length of barbed surgical thread. Further, according to an embodiment, removing the tube from under the skin may involve pulling on the proximal end or distal end of the tube at the respective entry point or exit point of the skin.

Further, according to an embodiment of the invention, there is provided an apparatus comprising: a flexible tube having an inner cavity, a proximal end, and a distal end; a cannula having an inner cavity, a proximal end, and a sharp-tipped distal end; a length of barbed surgical thread, a first portion of which is to be positioned in the interior cavity of the tube and extend beyond the distal end of the tube, and a second portion of which is to be positioned outside the proximal end of the tube; a connector; hair coupled via the connector to the second portion of the length of barbed surgical thread, whereupon insertion of the cannula and the tube under the skin, and the subsequent removal of the cannula from the tube, leaves the tube in position under the skin to accept the first portion of the length of barbed surgical thread which, when the tube is subsequently removed, secures a hold to tissue under the skin with the connector in a position above the skin with the hair coupled thereto.

Embodiment 5 is illustrated in FIG. 5A, FIG. 5B, FIG. 5C, FIG. 5D, and FIG. 5E. These figures show a series of operational steps and associated equipment for implanting hair. FIG. 5A shows a slightly curved sharp tipped cannula 550 attached to a tube 555 attached to the exterior of the cannula 550 that has been inserted (aided in part by the handle 545) under the skin 500. FIG. 5B shows the cannula 550 with handle 545 removed and the tube 555 remaining, effectively creating a tunnel between an insertion opening and an exit opening. FIG. 5C shows a complete assembly comprised of hair 510, a connector 520, and a surgical thread 530; where the surgical thread has been advanced through the proximal end of the tube 555 and exiting the distal end of the tube 555. In FIG. 5D, the tube 555 is removed leaving the surgical thread and the surgical thread is advanced until the connector 520 is either touching or nearly touching the skin 500. In FIG. 5E the surgical thread is trimmed at its distal end to be flush with or slightly below the skin. Thus, according to an embodiment, the cannula may be arcuate, curved, or form a smoothly rounded bend along its length from the proximal end to the distal end.

Figure 6A:
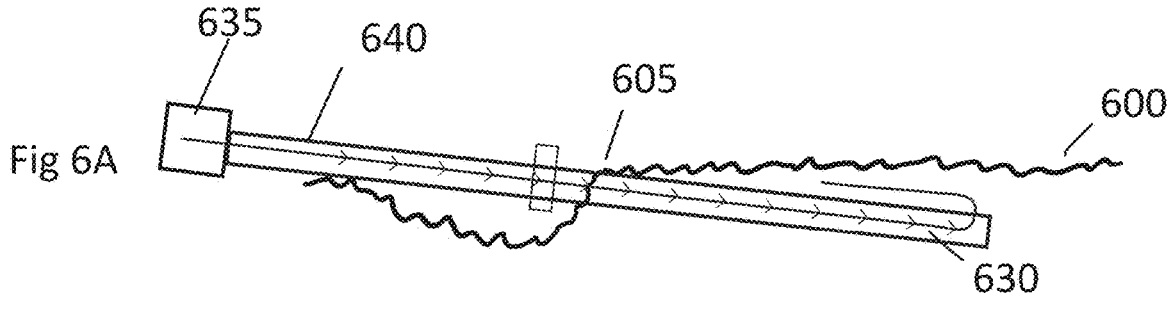
FIGS. 6A, 6B, 6C, 6D, and 6E are a series of diagrams showing the sequence of operational steps to implant hair in accordance with an embodiment of the invention.
Figure 6B:
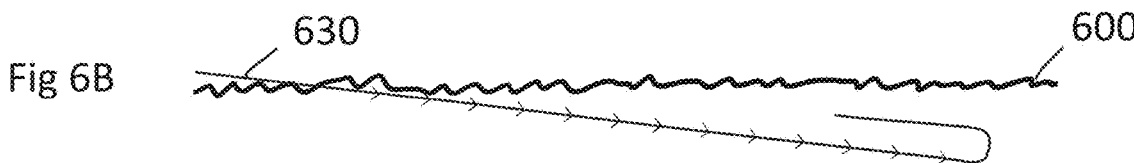
Figure 6C:
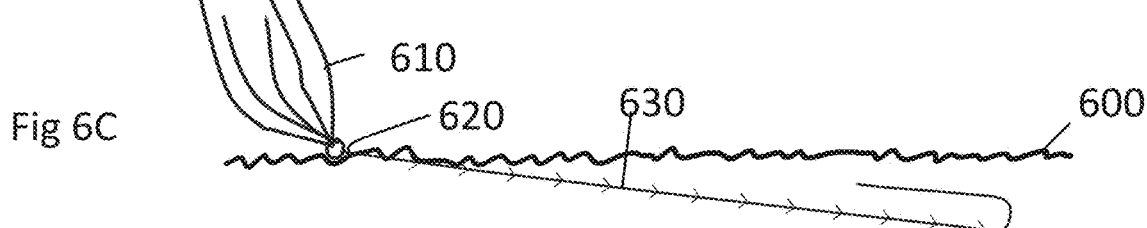
Figure 6D:
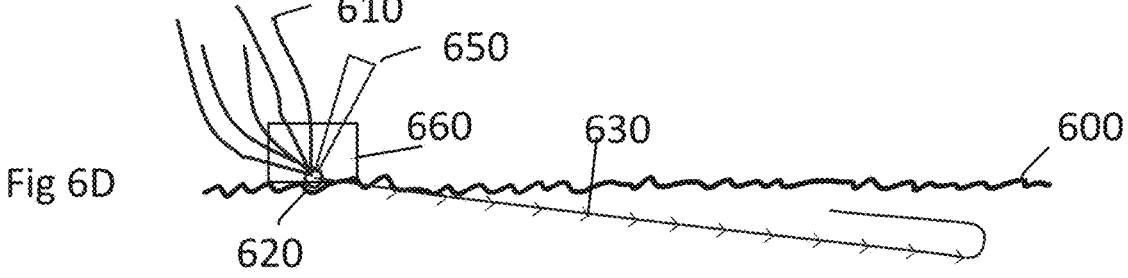

Embodiment 6 is illustrated in FIG. 6A, FIG. 6B, FIG. 6C, FIG. 6D, and FIG. 6E. These figures show a series of operational steps and associated equipment for implanting hair. The entry point 605 is prepared by inserting a straight needle to create a hole. FIG. 6A shows a blunt tipped cannula 640 and cannula handle 635 with a surgical thread 630 attached to the cannula, which has been inserted under the skin 600, through the hole created at the entry point 605. FIG. 6B shows the cannula 640 removed and the surgical thread 630 remaining in place under the skin. FIG. 6C shows hair that is mechanically coupled via a removable fastener or a permanent means (such as mechanical crimp/bead, or glue or chemical/thermal fusion or combination thereof) to the proximal end of the surgical thread, creating a connector 620. In the gluing embodiment shown in FIG. 6D, it may require a thermal stimulation element 650 and a temporary holding fixture 660 to give the glue sufficient time to cure.

7
8

Figure 6E:
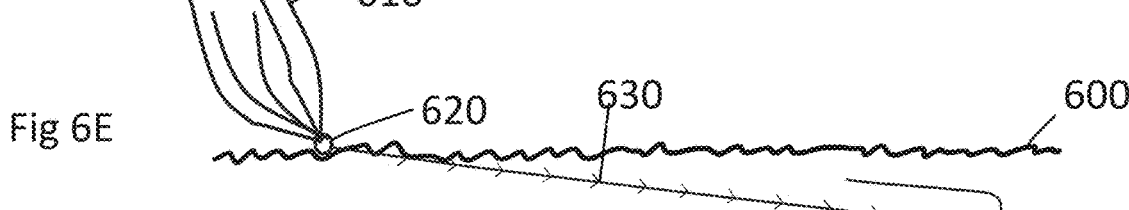

After the curing has been completed the temporary holding fixture is removed. FIG. 6E shows the hair implant (hair 610, connector 620 and surgical thread 630) in position.

Figure 7A:
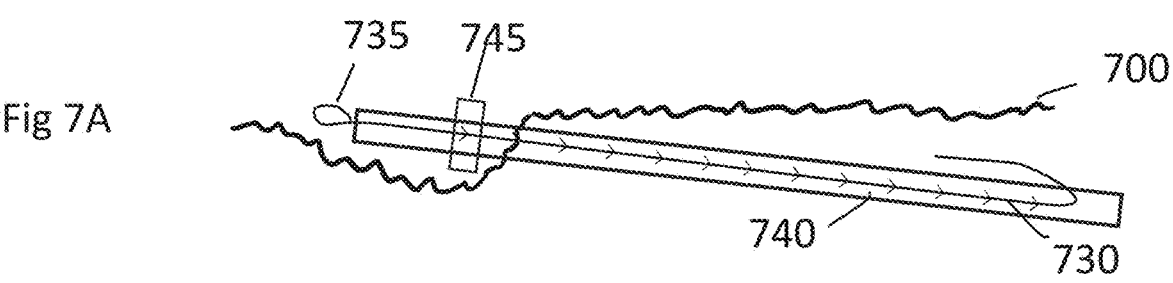
FIGS. 7A, 7B, 7C, and 7D are a series of diagrams showing the sequence of operational steps to implant hair in accordance with an embodiment of the invention.
Figure 7B:
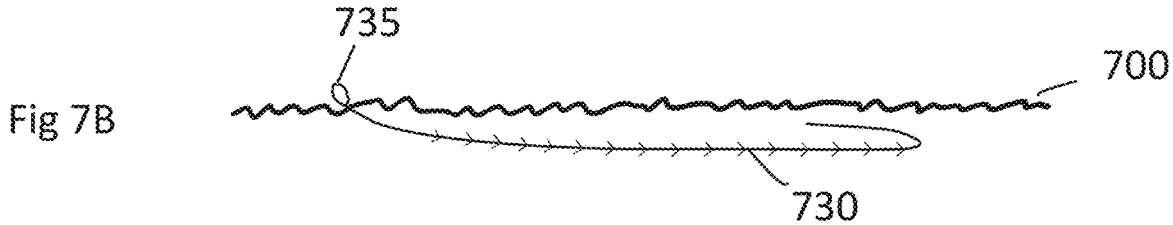
Figure 7C:
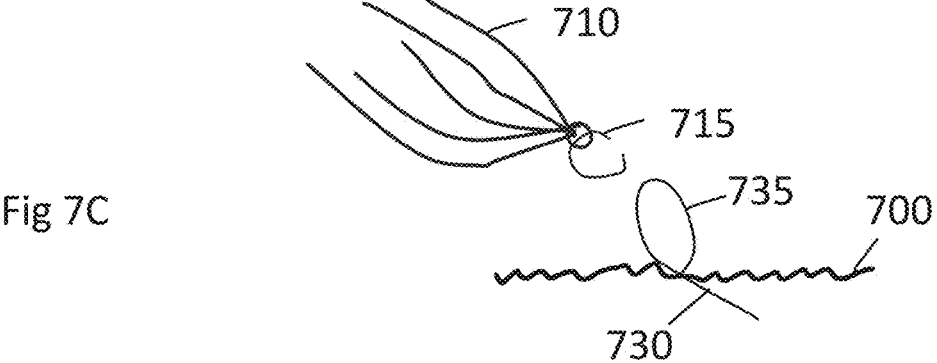
Figure 7D:
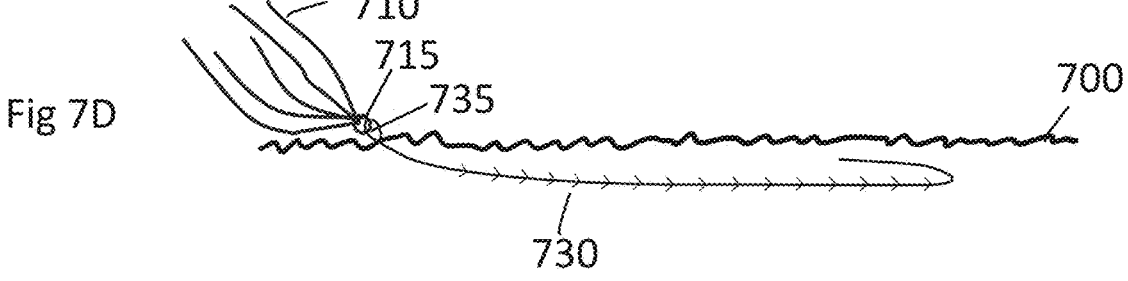

Embodiment 7 is illustrated in FIG. 7A, FIG. 7B, FIG. 7C, and FIG. 7D. These figures show a series of operational steps and associated equipment for implanting hair. FIG. 7A shows a blunt tipped cannula 740 with a surgical thread attached to the cannula, inserted under the skin 700. As in earlier blunt tipped cannula embodiment the insertion point and associated entry hole is first created by a needle. Notably the surgical thread 730 has a loop 735 at its proximal end. FIG. 7B shows the cannula 740 removed and the surgical thread 730 remaining in place under the skin. FIG. 7C shows hair 710 that contains a connector 715 that can be connected to surgical thread loop 735. FIG. 7D shows a hair implant (hair 710, connector 715 and surgical thread 730) fully installed, where the connector 715 is attached to surgical thread loop 735.

Embodiment 8 is illustrated in FIG. 8A, FIG. 8B, FIG. 8C, FIG. 8D, 8E, and FIG. 8F. These figures show a series of operational steps and associated equipment for implanting hair. FIG. 8A shows a blunt tipped cannula 840 with a folded barbed surgical thread attached to the cannula by a doughnut shaped elastomeric element 850, with the distal end of the cannula partially inserted under the skin 800. The surgical thread enters the proximal opening of the cannula and exits at the distal end and is folded back. As in earlier blunt tipped cannula embodiments the insertion point and associated entry hole is first created by a needle. As shown in FIG. 8B, as the cannula is advanced under the skin the FIG. 8C shows the cannula 840 removed and a portion of the surgical thread 830 remaining in place under the skin, with the two ends still available above the surface of the skin. FIG. 8D shows hair 810 that contains a connector 811 available to be engaged with the exposed ends of the inserted surgical thread. In FIG. 8E, the two exposed ends are tied to the connector 811, thereby creating a connection as depicted at 820. In FIG. 8E, the loose ends of the surgical threads are cut and the installation of the hair implant is completed. An alternative to the connector proposed is to construct the connector such that it may be disconnected, for example where a first loop on the end for the surgical thread is engaged to a disconnectable jeweler's loop. The advantage this provides is that the system is reconfigurable to different colors, lengths, densities, etc. per the desires of the person.

Thus, according to an embodiment of the invention, there is provided a method for attaching hair to a human, comprising: inserting a surgical thread through a cannula so that a first barbed portion of the surgical thread extends from a proximal end of the cannula through an inner cavity of the cannula to a distal end of the cannula, a second smooth portion of the surgical thread exits the distal end of the cannula and extends from the first portion outside and along an exterior surface of the cannula to beyond the proximal end of the cannula, and a third smooth portion of the surgical thread extends from the first portion to beyond the proximal end of the cannula; inserting the distal end of the cannula through an entry point of the skin of the human; advancing the cannula under the skin until the proximal end of the cannula is near the entry point of the skin; removing the cannula from under the skin, leaving in position under the skin the first barbed portion of the surgical thread which secures a hold to tissue under the skin; and attaching hair to the second and third smooth portions of the length of surgical thread. In an embodiment, the second smooth portion of the surgical thread that exits the distal end of the cannula and extends from the first portion outside and along an exterior surface of the cannula to beyond the proximal end of the cannula passes through a doughnut-shaped elastomeric element, an interior surface of which is slidably coupled to an outside surface of the cannula.

Further, according to an embodiment of the invention, there is provided an apparatus comprising: a cannula having an inner cavity, a proximal end, and a distal end; a length of surgical thread, a first barbed portion of which extends from a proximal end of the cannula through an interior cavity of the cannula to a distal end of the cannula, a second smooth portion of which exits the distal end of the cannula and extends from the first portion outside and along an exterior surface of the cannula to beyond the proximal end of the cannula, and a third smooth portion of which extends from the first portion to beyond the proximal end of the cannula; and hair coupled to the second and third smooth portions of the surgical thread, whereupon insertion and removal of the cannula from under the skin of a human leaves in position under the skin the first barbed portion of the surgical thread which secures a hold to tissue under the skin. This embodiment may include a doughnut-shaped elastomeric element, an interior surface of which is slidably coupled to an outside surface of the cannula, wherein the second smooth portion of the surgical thread that exits the distal end of the cannula and extends from the first portion outside and along the exterior surface of the cannula to beyond the proximal end of the cannula passes through the doughnut-shaped elastomeric element.

Figures 9A, 9B, 9C, 9D:
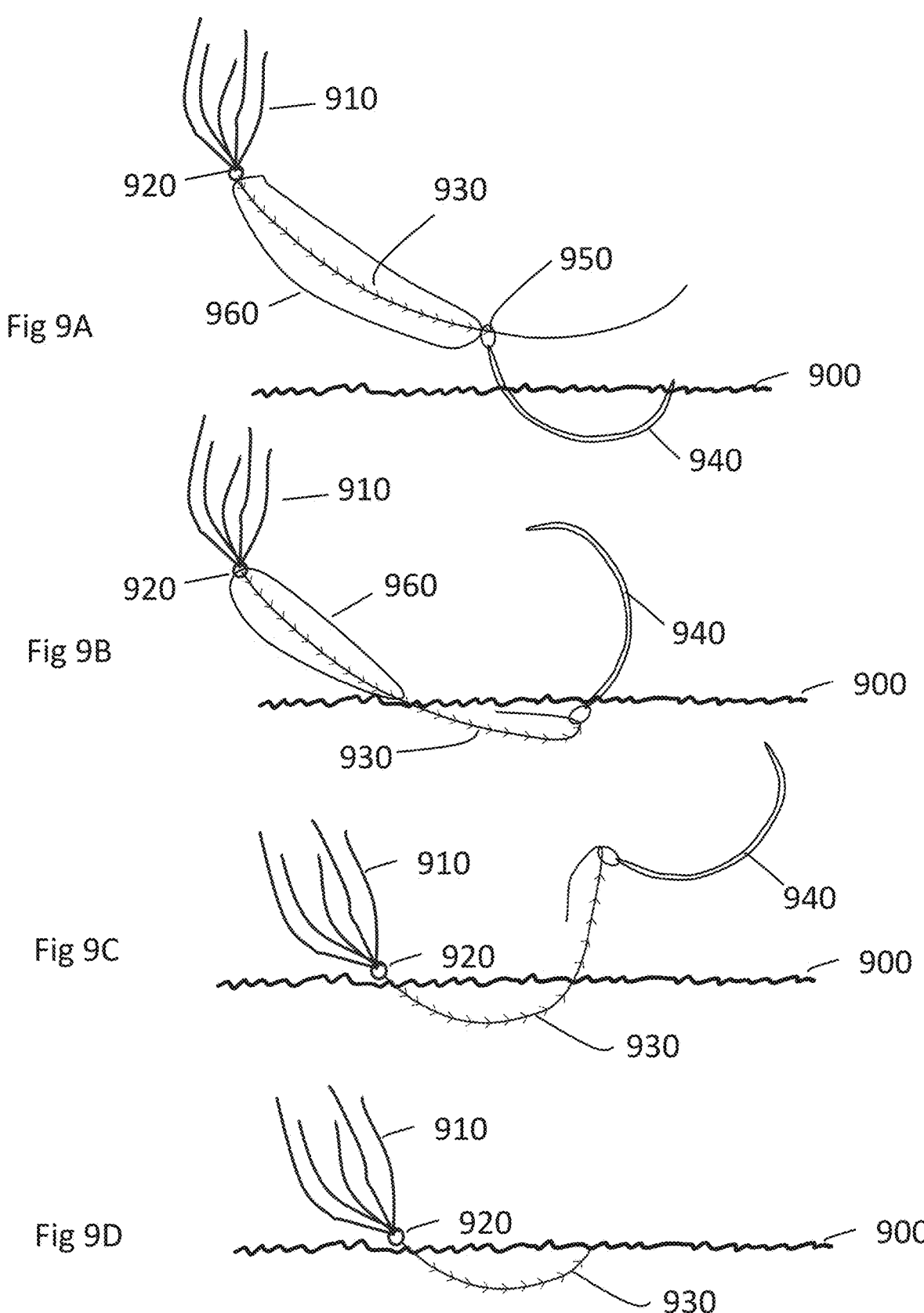
FIGS. 9A, 9B, 9C, and 9D are a series of diagrams showing the sequence of operational steps to implant hair in accordance with an embodiment of the invention.

Embodiment 9 is illustrated in FIG. 9A, FIG. 9B, FIG. 9C, and FIG. 9D. These figures show a series of operational steps and associated equipment for implanting hair. FIG. 9A shows a curved needle 940 with a loop 950 on its proximal end. A partially barbed surgical thread is inserted into the loop attached to the surgical thread at a location 950. A protective cover (e.g., a plastic or paper sleeve or bag) 960 covers the barbed portion of the surgical thread, preventing the barbed thread from becoming tangled with the hair. As the surgical thread is inserted and pulled under the skin, the cover 960 can be torn away or slides backwards along the barbed surgical thread so that no part of the cover is inserted under the skin. Alternatively, or additionally, a protective cover may cover the hair 910 for the same purpose. The surgical thread is part of a hair implant which is comprised of a hair 910 attached to said surgical thread 930 via a connector 920. In FIG. 9B the needle is advanced to exit the skin and pull the surgical thread under the skin 900. In FIG. 9C the needle is completely removed from the skin and has advanced the surgical thread such that the connector 920 is touching or nearly touching the surface of the skin 900. In FIG. 9D the surgical thread at the distal end is trimmed such that the end is flush with or under the surface of the skin 900.

Figures 10A, 10B, 10C, 10D:
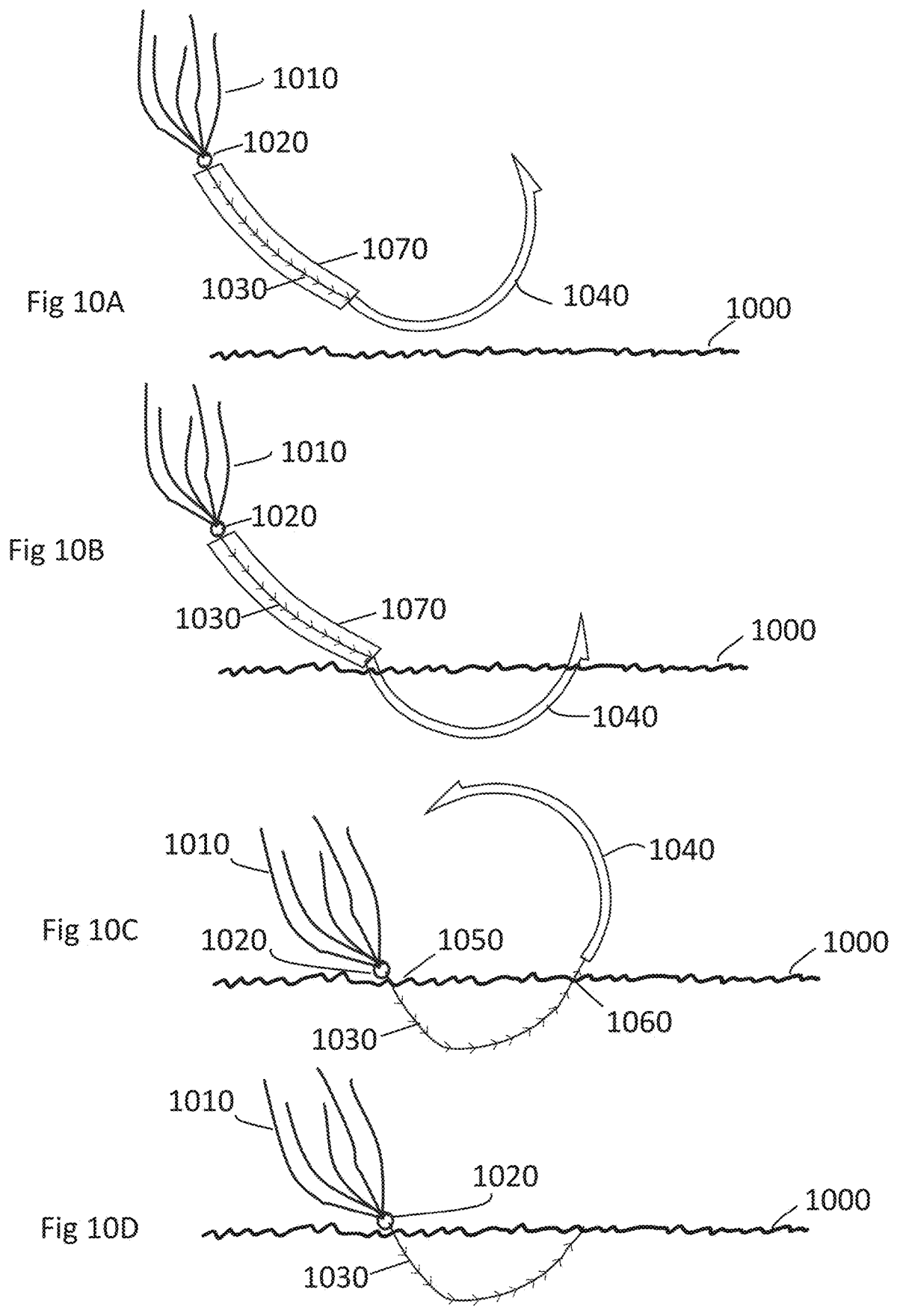

Embodiment 10 is illustrated in FIG. 10A, FIG. 10B, 10C, and FIG. 10D. These figures show a series of operational steps and associated equipment for implanting hair. FIG. 10A shows a barbed surgical thread 1030 attached to the end of a curved needle 1040. A tear-away plastic baggie 1070 covers the barbed portion of the surgical thread, preventing the barbed thread from being tangled with the hair. Furthermore FIG. 10A shows that the proximal end of the surgical thread is attached to a hair 1010 via a connector 1020. In FIG. 10B the distal end of the curved needle 1040 is inserted into the skin at a first point 1050 and advanced to exit the skin at a second point 1060. The surgical thread is advanced through the distal opening until the connector 1020 is touching or nearly touching the skin 1000. In FIG. 10C the extra length of the surgical thread at the distal end is trimmed, such that the end is flush or just beneath the skin 1000.

Thus, according to an embodiment of the invention, there is provided a method for attaching hair to a human, comprising: coupling a first portion of a surgical thread to a proximal end of a needle, leaving a barbed portion of the surgical thread trailing the proximal end of the needle; inserting a distal end of the needle through an entry point of the skin of the human; advancing the needle under the skin until first the distal end and then the proximal end of the needle emerge from an exit point of the skin of the human and a first length of the barbed portion of the surgical thread is pulled under the skin while a second, remaining length of the barbed portion of the surgical thread remains above the skin; decoupling surgical thread from the needle, leaving under the skin the first length of the barbed portion of the surgical thread to secure a hold to tissue under the skin and leaving above the skin the second length of the barbed portion of the surgical thread; and attaching hair to the second length of the second barbed portion of the surgical thread.

Embodiment 11 is illustrated in FIG. 11A, FIG. 11B, FIG. 11C, FIG. 11D, FIG. 11E, FIG. 11F, and FIG. 11G. These figures show a series of operational steps and associated equipment for implanting hair. FIG. 11A shows a sharp tipped cannula 1140 with a tube 1150 attached (on the outside) prior to insertion under the skin 1100. FIG. 11B shows the cannula 1140 and the attached tube 1150 inserted under the skin 1100 at entrance point 1180 and advance to an exit point 1190. FIG. 11C shows the cannula 1140 removed and the tube 1150 remaining, effectively creating a tunnel between an insertion opening and the exit opening. FIG. 11D shows a hair implant comprised of hair 1110, a connector 1120, and a barbed surgical thread 1130; where the barbed surgical thread has been advanced through the proximal end of the tube 1150 and exiting the distal end of the tube 1150. In FIG. 11E, the tube is removed from the exit point leaving the barbed surgical thread. In FIG. 11F the barbed surgical thread 1130 is advanced on the exposed distal end, until the connector 1120 is either touching or nearly touching the skin 1100. Hair 1160 is then attached to the barbed surgical thread 1130 forming a connection 1170. As discussed in previous embodiments that connector may be formed in a number of ways (e.g., glue, mechanical crimping, etc.) such that the connector touching or nearly touching the skin 1100. In FIG. 11G the excess surgical thread is trimmed at its distal end to be flush with or slightly below the skin 1100.

Thus, according to an embodiment of the invention, there is provided a method for attaching hair to a human, comprising: inserting and advancing a sharp-tipped distal end of a cannula through an inner cavity of a flexible tube until the distal end of the cannula projects beyond a distal end of the tube; inserting the distal end of the cannula and the distal end of the tube through an entry point of the skin of the human; advancing the cannula and tube under the skin until a proximal end of the cannula and a proximal end of the tube is near the entry point of the skin and the sharp-tipped distal end of the cannula pierces the skin of the human at an exit point that is different than the entry point and the distal ends of the cannula and the tube project beyond the exit point; retracting the cannula from the tube via the proximal end of the tube, leaving the tube in position under the skin; inserting a length of barbed surgical thread through the tube so that a first portion of the length of barbed surgical thread extends through the tube and beyond the distal end of the tube and a second portion of the length of barbed surgical thread extends beyond the proximal end of the tube; removing the tube from under the skin, leaving in position under the skin the first portion of the length of barbed surgical thread which secures a hold to tissue under the skin; and attaching hair to the second portion of the length of barbed surgical thread and to the first portion of the length of barbed surgical thread that extends beyond the distal end of the tube. Further, according to an embodiment, removing the tube from under the skin may involve pulling on the proximal end or distal end of the tube at the respective entry point or exit point of the skin.

Further, according to an embodiment of the invention, there is provided an apparatus comprising: a flexible tube having an inner cavity, a proximal end, and a distal end; a cannula having an inner cavity, a proximal end, and a sharp-tipped distal end; a length of barbed surgical thread, a first portion of which is to be positioned in the interior cavity of the tube and extend beyond the distal end of the tube, and a second portion of which is to be positioned outside the proximal end of the tube; a connector; hair coupled via the connector to the second portion of the length of barbed surgical thread, whereupon insertion of the cannula and the tube under the skin, and the subsequent removal of the cannula from the tube, leaves the tube in position under the skin to accept the first portion of the length of barbed surgical thread which, when the tube is subsequently removed, secures a hold to tissue under the skin with the connector in a position above the skin with the hair coupled thereto; and a second connector coupled to the first portion of the length of barbed surgical thread that extends beyond the distal end of the tube, to which to attach hair.

Figures 12A, 12B, 12C, 12D, 12E:
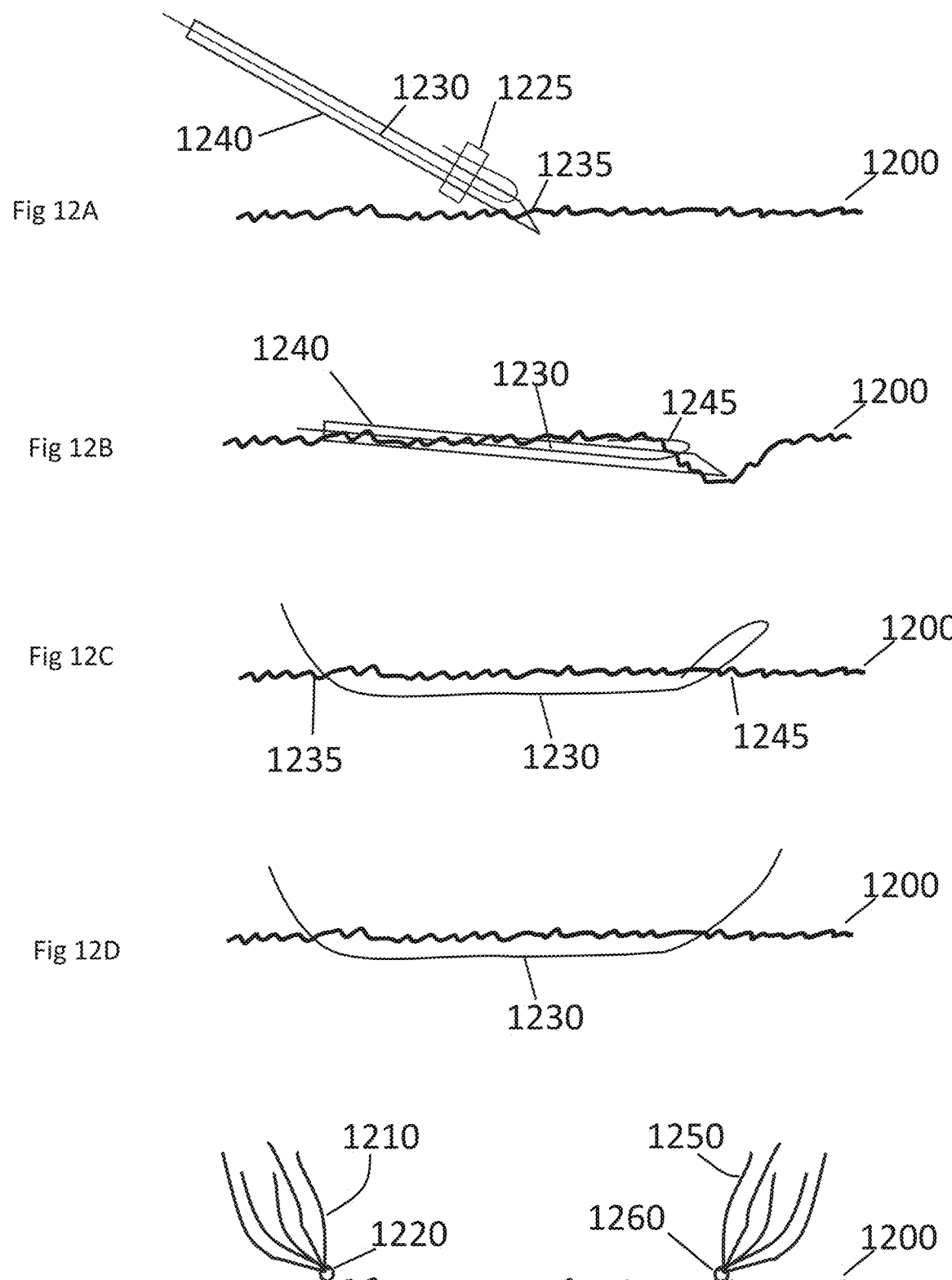
FIGS. 12A, 12B, 12C, 12D, and 12E are a series of diagrams showing the sequence of operational steps to implant hair in accordance with an embodiment of the invention.

Embodiment 12 is illustrated in FIG. 12A, FIG. 12B, FIG. 12C, FIG. 12D, and FIG. 12E. These figures show a series of operational steps and associated equipment or implanting hair. FIG. 12A shows a cannula 1240 containing a smooth surgical fiber. The distal end of the cannula 1240 is inserted into the skin 1200 at insertion point 1235. In FIG. 12B the cannula is advance under the skin to an exit point 1245, facilitated by depressing the skin just after the desired exit point. In FIG. 12C the cannula 1240 is extracted through the exit point 1245, leaving the smooth thread 1230 ends exposed. In FIG. 12D the exposed ends of the smooth thread are straightened. In FIG. 12E hair 1210 is attached at the proximal end via a first connector 1220 (as described in other embodiments, then hair 1250 is attached at the distal end via a second connector 1260, such that both connectors are touching or nearly touching the skin. Any excessive thread is trimmed away at each end. This embodiment has a different anchoring principle than embodiments 1 through 11. In embodiment 12 hair 1210 acts as an anchor for hair 1250, and reciprocally hair 1250 acts as an anchor for hair 1210. Therefore, it does not require a barbed surgical thread. One of the advantages of this embodiment is that it costs less than the other embodiments because a smooth surgical thread is approximately 2% of the cost of a barbed surgical thread. Another benefit of using a smooth surgical thread is that lifetime under load is better understood and may be considerably longer.

Thus, according to an embodiment of the invention, there is provided a method for attaching hair to a human, comprising: inserting and advancing a sharp-tipped distal end of a cannula through an inner cavity of a flexible tube until the distal end of the cannula projects beyond a distal end of the tube; inserting the distal end of the cannula and the distal end of the tube through an entry point of the skin of the human; advancing the cannula and tube under the skin until a proximal end of the cannula and a proximal end of the tube is near the entry point of the skin and the sharp-tipped distal end of the cannula pierces the skin of the human at an exit point that is different than the entry point and the distal ends of the cannula and the tube project beyond the exit point; retracting the cannula from the tube via the proximal end of the tube, leaving the tube in position under the skin; inserting a length of smooth surgical thread through the tube so that a first portion of the length of smooth surgical thread extends through the tube and beyond the distal end of the tube and a second portion of the length of smooth surgical thread extends beyond the proximal end of the tube; removing the tube from under the skin, leaving in position under the skin the first portion of the length of smooth surgical thread; attaching hair to the second portion of the length of barbed surgical thread; and attaching hair to the first portion of the length of barbed surgical thread that extends beyond the distal end of the tube.

Further, according to an embodiment of the invention, there is provided an apparatus comprising: a flexible tube having an inner cavity, a proximal end, and a distal end; a cannula having an inner cavity, a proximal end, and a sharp-tipped distal end; a length of smooth surgical thread, a first portion of which is to be positioned in the interior cavity of the tube and extend beyond the distal end of the tube, and a second portion of which is to be positioned outside the proximal end of the tube; a connector; hair coupled via the connector to the second portion of the length of smooth surgical thread; a second connector; and hair coupled via the second connector to the first potion of the smooth surgical thread that extends beyond the distal end of the tube, whereupon insertion of the cannula and the tube under the skin, and the subsequent removal of the cannula from the tube, leaves the tube in position under the skin to accept the first portion of the length of smooth surgical thread which, when the tube is subsequently removed, is positioned under the skin.

Embodiment 13 is illustrated in FIG. 13A, FIG. 13B, FIG. 13C, FIG. 13D, and FIG. 13E. These figures show a series of operational steps and associated equipment for implanting hair. FIG. 13A shows a curved needle with a smooth surgical thread 1310 attached to the proximal end of said needle, ready to be inserted into the skin 1300. In FIG. 13B the curved need is inserted into an insertion point 1335 and advanced to an exit point 1345. In FIG. 13C the curved needle is further advanced such that the entirety of the needle has exited the skin and sufficient smooth surgical fiber is available for the next step. In FIG. 13D hair 1320 is attached at the proximal end via a first connector 1325 (as described in other embodiments, then hair 1350 is attached at the distal end via a second connector 1355, such that both connectors are touching or nearly touching the skin. In FIG. 13E the excess surgical fiber is trimmed and the needle is disengaged, completing a dual hair implant installation. The advantage with this embodiment is a reduction in installation time, the potential for higher density installations. Furthermore, it is envisioned that this approach may be amenable to semi-automation.

Thus, according to an embodiment of the invention, there is provided a method for attaching hair to a human, comprising: coupling a surgical thread to a proximal end of a needle; inserting a distal end of the needle through an entry point of the skin of the human; advancing the needle under the skin until first the distal end and then the proximal end of the needle emerge from an exit point of the skin of the human and a first portion of surgical thread is pulled under the skin and through and extending beyond the exit point while a second, remaining second portion of the surgical thread remains above the skin and beyond the entry point; decoupling the surgical thread from the needle; and attaching hair to both the first potion of surgical thread extending beyond the exit point and to the second portion of the surgical thread that remains above the skin and beyond the entry point.

Embodiment 14 is illustrated in FIG. 14A, FIG. 14B, FIG. 14C, and FIG. 14D. These figures show a series of operational steps and associated equipment for implanting hair. This is essentially the same as embodiment 13 with the exception that a sub-assembly, consisting of hair 1420 with smooth surgical thread 1410 coupled to hair 1420 via a connector 1425 with opposite end of said surgical thread 1410 connected to a curved needle 1440, is prefabricated and is ready to install. Hair 1450 and associated connector 1455 are still installed by the practitioner in real time. The advantage is a reduction in installation time. Thus, attaching hair to the second portion of the surgical thread that remains above the skin and beyond the entry point as described in the previous embodiment can be carried out as a first or subsequent step in the process rather than a later or last step in the process.

Embodiment 15 is illustrated in FIG. 15A, FIG. 15B, FIG. 15C, and FIG. 15D. These figures show a series of operational steps and associated equipment for implanting hair. This is essentially the same as embodiment 14 with the exception that hair 1420 is replaced with an anchor element 1570. This embodiment has the advantage of making it easier to find suitable installation sites that require sufficient clearance for only a single hair element.

Although the subject matter has been described in language specific to structural features and/or methodological acts, it is to be understood that the subject matter is not necessarily limited to the specific features or acts described above. Rather, the specific features and acts described above are disclosed as example embodiments.

What is claimed is:

1. A method for attaching hair to a human, comprising:
inserting a length of barbed surgical thread through a cannula so that a first portion including a distal end of the length of barbed surgical thread is near a distal end of the cannula and a second portion of the length of barbed surgical thread is outside the proximal end of the cannula;
inserting the distal end of the cannula through an entry point of the skin of the human;
advancing the cannula under the skin until the proximal end of the cannula is near the entry point of the skin;
removing the cannula from under the skin, leaving in position under the skin the first portion of the length of barbed surgical thread which secures a hold to tissue under the skin; and
attaching hair to the second portion of the length of barbed surgical thread.

2. The method of claim 1 wherein the distal end of the cannula comprises a sharp tip, and wherein:
inserting the distal end of the cannula through an entry point of the skin of the human comprises the sharp-tipped distal end of the cannula piercing the skin of the human at the entry point;
removing the cannula from under the skin comprises the sharp-tipped distal end of the cannula piercing the skin of the human at an exit point that is different than the entry point and pulling on the distal end of the cannula at the exit point of the skin.

3. The method of claim 2 wherein the cannula comprises a handle removably coupled to the proximal end of the cannula, and wherein:

inserting the distal end of the cannula through an entry point of the skin and advancing the cannula under the skin until the proximal end of the cannula is near the entry point of the skin comprises applying pressure on the handle of the cannula to effect insertion of the distal end of the cannula through the entry point of the skin and advancement of the cannula under the skin until the proximal end of the cannula is near the entry point of the skin; and further comprising removing the handle from the proximal end of the cannula before removing the cannula from under the skin comprises the sharp-tipped distal end of the cannula piercing the skin of the human at an exit point that is different than the entry point and pulling on the distal end of the cannula at the exit point of the skin.

4. The method of claim 1, wherein a protective cover encompasses at least a portion of the hair, the method further comprising removing the protective cover after the steps of removing the cannula from under the skin and attaching hair to the second portion of the length of barbed surgical thread.

5. A method for attaching hair to a human, comprising:

inserting a surgical thread through a cannula so that a first barbed portion of the surgical thread extends from a proximal end of the cannula through an inner cavity of the cannula to a distal end of the cannula, a second smooth portion of the surgical thread exits the distal end of the cannula and extends from the first portion outside and along an exterior surface of the cannula to beyond the proximal end of the cannula, and a third smooth portion of the surgical thread extends from the first portion to beyond the proximal end of the cannula;

inserting the distal end of the cannula through an entry point of the skin of the human;

advancing the cannula under the skin until the proximal end of the cannula is near the entry point of the skin;

removing the cannula from under the skin, leaving in position under the skin the first barbed portion of the surgical thread which secures a hold to tissue under the skin; and attaching hair to the second and third smooth portions of the length of surgical thread.

6. The method of claim 5, wherein the second smooth portion of the surgical thread that exits the distal end of the cannula and extends from the first portion outside and along an exterior surface of the cannula to beyond the proximal end of the cannula passes through a doughnut-shaped elastomeric element, an interior surface of which is slidably coupled to an outside surface of the cannula.

* * * * *